US010228487B2

(12) United States Patent
Mastronardi

(10) Patent No.: US 10,228,487 B2
(45) Date of Patent: Mar. 12, 2019

(54) RAPIDLY RELOCATABLE MODULAR CARGO CONTAINER SCANNER

(71) Applicant: American Science and Engineering, Inc., Billerica, MA (US)

(72) Inventor: Richard Mastronardi, Medfield, MA (US)

(73) Assignee: American Science and Engineering, Inc., Billerica, MA (US)

( * ) Notice: Subject to any disclaimer, the term of this patent is extended or adjusted under 35 U.S.C. 154(b) by 137 days.

(21) Appl. No.: 15/307,473

(22) PCT Filed: May 15, 2015

(86) PCT No.: PCT/US2015/031115
§ 371 (c)(1),
(2) Date: Oct. 28, 2016

(87) PCT Pub. No.: WO2016/003547
PCT Pub. Date: Jan. 7, 2016

(65) Prior Publication Data
US 2017/0059739 A1    Mar. 2, 2017

Related U.S. Application Data

(60) Provisional application No. 62/018,787, filed on Jun. 30, 2014.

(51) Int. Cl.
*G01N 23/10* (2018.01)
*G01V 5/00* (2006.01)
*G01N 23/04* (2018.01)

(52) U.S. Cl.
CPC ............ *G01V 5/0025* (2013.01); *G01N 23/04* (2013.01); *G01N 23/10* (2013.01); *G01V 5/0008* (2013.01);

(Continued)

(58) Field of Classification Search
CPC ............ G01N 23/10; G01N 2223/045; G01N 2223/301; G01N 2223/3307;
(Continued)

(56) References Cited

U.S. PATENT DOCUMENTS

| 2,636,619 A | 4/1953 | Alexander |
| 3,275,831 A | 9/1966 | Martin |

(Continued)

FOREIGN PATENT DOCUMENTS

| EP | 0077018 A1 | 4/1983 |
| EP | 0919186 A2 | 6/1999 |

(Continued)

OTHER PUBLICATIONS

Gijeong Jang, Authorized officer Korean Intellectual Property Office, International Search Report—Application No. PCT/US2015/031115, dated Jul. 29, 2015, 10 pages, *together with the Written Opinion of the International Searching Authority*.
(Continued)

*Primary Examiner* — Thomas R Artman
(74) *Attorney, Agent, or Firm* — Novel IP

(57) ABSTRACT

An X-ray cargo inspection system and method. A lead-in conveyor on a first trailer receives a cargo container for inspection. An inspection module disposed on a second trailer then scans the cargo container with penetrating radiation, detects penetrating radiation that has interacted with the cargo container, and produces an inspection signal. An exit conveyor disposed on a third trailer projects the cargo container following scanning. The inspection module may contain transmission or scatter detectors, or both. Multiple lead-in conveyors may serve to load additional cargo containers for subsequent scanning by the inspection module.

19 Claims, 3 Drawing Sheets

(52) U.S. Cl.
CPC . *G01N 2223/639* (2013.01); *G01N 2223/643* (2013.01)

(58) Field of Classification Search
CPC ..... G01N 2223/3308; G01N 2223/639; G01N 2223/643; G01V 5/0008; G01V 5/0016; G01V 5/0069
See application file for complete search history.

(56) References Cited

U.S. PATENT DOCUMENTS

| | | |
|---|---|---|
| 3,374,355 A | 3/1968 | Parratt |
| 3,439,166 A | 4/1969 | Chope |
| 3,837,502 A | 9/1974 | Hornagold |
| 3,904,923 A | 9/1975 | Schwartz |
| 4,045,672 A | 8/1977 | Watanabe |
| 4,164,138 A | 8/1979 | Burkhart |
| 4,239,969 A | 12/1980 | Galetta |
| 4,242,583 A | 12/1980 | Annis |
| 4,658,408 A | 4/1987 | Amor |
| 5,014,293 A | 5/1991 | Boyd |
| 5,041,728 A | 8/1991 | Spacher |
| 5,065,418 A | 11/1991 | Bermbach |
| 5,181,234 A | 1/1993 | Smith |
| 5,185,778 A | 2/1993 | Magram |
| 5,197,088 A | 3/1993 | Vincent |
| 5,202,932 A | 4/1993 | Cambier |
| 5,259,012 A | 11/1993 | Baker |
| 5,363,940 A | 11/1994 | Fahrion |
| 5,493,596 A | 2/1996 | Annis |
| 5,503,424 A | 4/1996 | Agopian |
| 5,600,303 A | 2/1997 | Husseiny |
| 5,606,167 A | 2/1997 | Miller |
| 5,692,028 A | 11/1997 | Geus |
| 5,692,029 A | 11/1997 | Husseiny |
| 5,842,578 A | 12/1998 | Cordeiro |
| 5,909,478 A | 6/1999 | Polichar |
| 5,910,973 A | 6/1999 | Grodzins |
| 5,940,468 A | 8/1999 | Huang |
| 5,974,111 A | 10/1999 | Krug |
| 6,056,671 A | 5/2000 | Marmer |
| 6,067,344 A | 5/2000 | Grodzins |
| 6,081,580 A | 6/2000 | Grodzins |
| 6,151,381 A | 11/2000 | Grodzins |
| 6,192,104 B1 | 2/2001 | Adams |
| 6,216,540 B1 | 4/2001 | Nelson |
| 6,220,099 B1 | 4/2001 | Marti |
| 6,249,567 B1 | 6/2001 | Rothschild |
| 6,292,533 B1 | 9/2001 | Swift |
| 6,301,327 B1 | 10/2001 | Martens |
| 6,320,933 B1 | 11/2001 | Grodzins |
| 6,347,132 B1 | 2/2002 | Annis |
| 6,418,194 B1 | 7/2002 | McPherson |
| 6,424,695 B1 | 7/2002 | Grodzins |
| 6,442,233 B1 | 8/2002 | Grodzins |
| 6,453,007 B2 | 9/2002 | Adams |
| 6,459,761 B1 | 10/2002 | Grodzins |
| 6,459,764 B1 | 10/2002 | Chalmers |
| 6,542,574 B2 | 4/2003 | Grodzins |
| 6,542,580 B1 | 4/2003 | Carver |
| 6,546,072 B1 | 4/2003 | Chalmers |
| 6,552,346 B2 | 4/2003 | Verbinski |
| 6,614,872 B2 | 9/2003 | Bueno |
| 6,621,888 B2 | 9/2003 | Grodzins |
| 6,658,087 B2 | 12/2003 | Chalmers |
| 6,665,373 B1 | 12/2003 | Kotowski |
| 6,702,459 B2 | 3/2004 | Barnes |
| 6,713,773 B1 | 3/2004 | Lyons |
| 6,843,599 B2 | 1/2005 | Le |
| 6,920,197 B2 | 7/2005 | Kang |
| 6,924,487 B2 | 8/2005 | Bolozdynya |
| 6,928,141 B2 | 8/2005 | Carver |
| 6,965,662 B2 | 11/2005 | Eppler |
| 7,010,094 B2 | 3/2006 | Grodzins |
| 7,046,768 B1 | 5/2006 | Gilevich |
| 7,099,434 B2 | 8/2006 | Adams |
| RE39,396 E | 11/2006 | Swift |
| 7,151,447 B1 | 12/2006 | Willms |
| 7,203,276 B2 | 4/2007 | Arsenault |
| 7,207,713 B2 | 4/2007 | Lowman |
| 7,215,738 B2 | 5/2007 | Muenchau |
| 7,218,704 B1 | 5/2007 | Adams |
| 7,322,745 B2 | 1/2008 | Agrawal |
| 7,366,282 B2 | 4/2008 | Peschmann |
| 7,369,643 B2 | 5/2008 | Kotowski |
| 7,379,530 B2 | 5/2008 | Hoff |
| 7,397,891 B2 | 7/2008 | Johnson |
| 7,400,701 B1 | 7/2008 | Cason |
| 7,417,440 B2 | 8/2008 | Peschmann |
| 7,418,077 B2 | 8/2008 | Gray |
| 7,453,987 B1 | 11/2008 | Richardson |
| 7,471,764 B2 | 12/2008 | Kaval |
| 7,483,510 B2 | 1/2009 | Carver |
| 7,486,768 B2 | 2/2009 | Allman |
| 7,505,556 B2 | 3/2009 | Chalmers |
| 7,505,562 B2 | 3/2009 | Dinca |
| 7,517,149 B2 | 4/2009 | Agrawal |
| 7,519,148 B2 | 4/2009 | Kotowski |
| 7,525,101 B2 | 4/2009 | Grodzins |
| 7,526,064 B2 | 4/2009 | Akery |
| 7,538,325 B2 | 5/2009 | Mishin |
| 7,551,715 B2 | 6/2009 | Rothschild |
| 7,551,718 B2 | 6/2009 | Rothschild |
| 7,555,099 B2 | 6/2009 | Rothschild |
| 7,579,845 B2 | 8/2009 | Peschmann |
| 7,593,506 B2 | 9/2009 | Cason |
| 7,593,510 B2 | 9/2009 | Rothschild |
| 7,660,388 B2 | 2/2010 | Gray |
| 7,720,195 B2 | 5/2010 | Allman |
| 7,742,568 B2 | 6/2010 | Smith |
| 7,769,133 B2 | 8/2010 | Carver |
| 7,783,004 B2 | 8/2010 | Kotowski |
| 7,783,005 B2 | 8/2010 | Kaval |
| 7,817,776 B2 | 10/2010 | Agrawal |
| 7,856,081 B2 | 12/2010 | Peschmann |
| 7,860,213 B2 | 12/2010 | Akery |
| 7,864,920 B2 | 1/2011 | Rothschild |
| 7,876,879 B2 | 1/2011 | Morton |
| 7,876,880 B2 | 1/2011 | Kotowski |
| 7,915,596 B2 | 3/2011 | Clothier |
| 7,924,979 B2 | 4/2011 | Rothschild |
| 7,928,400 B1 | 4/2011 | Diawara |
| 7,963,695 B2 | 6/2011 | Kotowski |
| 7,982,191 B2 | 7/2011 | Friedman |
| 7,991,133 B2 | 8/2011 | Mills |
| 7,995,705 B2 | 8/2011 | Allman |
| 7,995,707 B2 | 8/2011 | Rothschild |
| 8,054,938 B2 | 11/2011 | Kaval |
| 8,059,781 B2 | 11/2011 | Agrawal |
| 8,073,099 B2 | 12/2011 | Niu |
| 8,135,110 B2 | 3/2012 | Morton |
| 8,138,770 B2 | 3/2012 | Peschmann |
| 8,170,177 B2 | 5/2012 | Akery |
| 8,194,822 B2 | 6/2012 | Rothschild |
| 8,243,876 B2 | 8/2012 | Morton |
| 8,275,091 B2 | 9/2012 | Morton |
| 8,275,092 B1 | 9/2012 | Zhang |
| 8,325,871 B2 | 12/2012 | Grodzins |
| 8,345,819 B2 | 1/2013 | Mastronardi |
| 8,356,937 B2 | 1/2013 | Kotowski |
| 8,385,501 B2 | 2/2013 | Allman |
| 8,389,942 B2 | 3/2013 | Morton |
| 8,428,217 B2 | 4/2013 | Peschmann |
| 8,433,036 B2 | 4/2013 | Morton |
| 8,439,565 B2 | 5/2013 | Mastronardi |
| 8,442,186 B2 | 5/2013 | Rothschild |
| 8,457,274 B2 | 6/2013 | Arodzero |
| 8,457,275 B2 | 6/2013 | Akery |
| 8,483,356 B2 | 7/2013 | Bendahan |
| 8,491,189 B2 | 7/2013 | Kotowski |
| 8,503,605 B2 | 8/2013 | Morton |
| 8,503,606 B2 | 8/2013 | Rothschild |
| 8,532,823 B2 | 9/2013 | McElroy |
| 8,579,506 B2 | 11/2013 | Morton |

(56) References Cited

U.S. PATENT DOCUMENTS

| | | |
|---|---|---|
| 8,582,720 B2 | 11/2013 | Morton |
| 8,644,453 B2 | 2/2014 | Morton |
| 8,668,386 B2 | 3/2014 | Morton |
| 8,674,706 B2 | 3/2014 | Peschmann |
| 8,687,765 B2 | 4/2014 | Kotowski |
| 8,690,427 B2 | 4/2014 | Mastronardi |
| 8,731,137 B2 | 5/2014 | Arroyo |
| 8,735,833 B2 | 5/2014 | Morto |
| 8,750,452 B2 | 6/2014 | Kaval |
| 8,750,454 B2 | 6/2014 | Gozani |
| 8,774,357 B2 | 7/2014 | Morton |
| 8,798,232 B2 | 8/2014 | Bendahan |
| 8,824,632 B2 | 9/2014 | Mastronardi |
| 8,831,176 B2 | 9/2014 | Morto |
| 8,837,670 B2 | 9/2014 | Akery |
| 8,840,303 B2 | 9/2014 | Morton |
| 8,842,808 B2 | 9/2014 | Rothschild |
| 8,861,684 B2 | 10/2014 | Al-Kofahi |
| 8,903,045 B2 | 12/2014 | Schubert |
| 8,903,046 B2 | 12/2014 | Morton |
| 8,908,831 B2 | 12/2014 | Bendahan |
| 8,929,509 B2 | 1/2015 | Morton |
| 8,958,526 B2 | 2/2015 | Morton |
| 8,971,485 B2 | 3/2015 | Morton |
| 8,971,487 B2 | 3/2015 | Mastronardi |
| 8,993,970 B2 | 3/2015 | Morton |
| 9,014,339 B2 | 4/2015 | Grodzins |
| 9,020,095 B2 | 4/2015 | Morton |
| 9,020,096 B2 | 4/2015 | Allman |
| 9,020,103 B2 | 4/2015 | Grodzins |
| 9,025,731 B2 | 5/2015 | Kotowski |
| 9,042,511 B2 | 5/2015 | Peschmann |
| 9,052,271 B2 | 6/2015 | Grodzins |
| 9,052,403 B2 | 6/2015 | Morton |
| 9,057,679 B2 | 6/2015 | Morton |
| 9,069,101 B2 | 6/2015 | Arroyo, Jr. |
| 9,086,497 B2 | 7/2015 | Bendahan |
| 9,099,279 B2 | 8/2015 | Rommel |
| 9,111,331 B2 | 8/2015 | Parikh |
| 9,117,564 B2 | 8/2015 | Rommel |
| 9,121,958 B2 | 9/2015 | Morton |
| 9,128,198 B2 | 9/2015 | Morton |
| 9,146,201 B2 | 9/2015 | Schubert |
| 9,158,027 B2 | 10/2015 | Morton |
| 9,207,195 B2 | 12/2015 | Gozani |
| 9,218,933 B2 | 12/2015 | Langeveld |
| 9,223,049 B2 | 12/2015 | Kotowski |
| 9,223,050 B2 | 12/2015 | Kaval |
| 9,223,052 B2 | 12/2015 | Morton |
| 9,257,208 B2 | 2/2016 | Rommel |
| 9,268,058 B2 | 2/2016 | Peschmann |
| 9,274,065 B2 | 3/2016 | Morton |
| 9,279,901 B2 | 3/2016 | Akery |
| 9,285,488 B2 | 3/2016 | Arodzero |
| 9,285,498 B2 | 3/2016 | Carver |
| 9,291,582 B2 | 3/2016 | Grodzins |
| 9,310,322 B2 | 4/2016 | Panesar |
| 9,310,323 B2 | 4/2016 | Bendahan |
| 9,316,760 B2 | 4/2016 | Bendahan |
| 9,329,285 B2 | 5/2016 | Gozani |
| 9,332,624 B2 | 5/2016 | Morton |
| 9,417,060 B1 | 8/2016 | Schubert |
| 9,465,135 B2 | 10/2016 | Morton |
| 9,466,456 B2 | 10/2016 | Rommel |
| 9,535,019 B1 | 1/2017 | Rothschild |
| 9,541,510 B2 | 1/2017 | Arodzero |
| 9,562,866 B2 | 2/2017 | Morton |
| 9,632,205 B2 | 4/2017 | Morton |
| 9,658,343 B2 | 5/2017 | Arodzero |
| 9,791,590 B2 | 10/2017 | Morton |
| 9,823,201 B2 | 11/2017 | Morton |
| 9,841,386 B2 | 12/2017 | Grodzins |
| 2002/0094064 A1 | 7/2002 | Zhou |
| 2003/0043964 A1 | 3/2003 | Sorenson |
| 2003/0068557 A1 | 4/2003 | Kumashiro |
| 2004/0051265 A1 | 3/2004 | Nadeau |
| 2004/0120454 A1 | 6/2004 | Ellenbogen |
| 2004/0141584 A1 | 7/2004 | Bernardi |
| 2004/0252024 A1 | 12/2004 | Huey |
| 2004/0258198 A1 | 12/2004 | Carver |
| 2005/0023479 A1 | 2/2005 | Grodzins |
| 2005/0024199 A1 | 2/2005 | Huey |
| 2005/0100135 A1 | 5/2005 | Lowman |
| 2005/0117683 A1 | 6/2005 | Mishin |
| 2005/0135668 A1 | 6/2005 | Polichar |
| 2005/0157842 A1 | 7/2005 | Agrawal |
| 2005/0169421 A1 | 8/2005 | Muenchau |
| 2005/0198226 A1 | 9/2005 | Delia |
| 2006/0027751 A1 | 2/2006 | Kurita |
| 2006/0056584 A1 | 3/2006 | Allman |
| 2006/0114477 A1 | 6/2006 | Cox |
| 2006/0140341 A1 | 6/2006 | Carver |
| 2006/0182221 A1 | 8/2006 | Bernhardt |
| 2006/0249685 A1 | 11/2006 | Tanaka |
| 2006/0257005 A1 | 11/2006 | Bergeron |
| 2006/0284094 A1 | 12/2006 | Inbar |
| 2007/0085010 A1 | 4/2007 | Letant |
| 2007/0140423 A1 | 6/2007 | Foland |
| 2007/0172129 A1 | 7/2007 | Tortora |
| 2007/0189454 A1 | 8/2007 | Georgeson |
| 2007/0210255 A1 | 9/2007 | Bjorkholm |
| 2007/0228284 A1 | 10/2007 | Polichar |
| 2007/0237293 A1 | 10/2007 | Singh |
| 2007/0280502 A1 | 12/2007 | Paresi |
| 2008/0037707 A1 | 2/2008 | Rothschild |
| 2008/0048872 A1 | 2/2008 | Frank |
| 2008/0084963 A1 | 4/2008 | Clayton |
| 2008/0128624 A1 | 6/2008 | Cooke |
| 2008/0159591 A1 | 7/2008 | Ruedin |
| 2008/0170670 A1 | 7/2008 | Bhatt |
| 2008/0197279 A1 | 8/2008 | Kang et al. .................. 250/306 |
| 2008/0198970 A1 | 8/2008 | Kirshner |
| 2008/0205594 A1 | 8/2008 | Bjorkholm |
| 2008/0230709 A1 | 9/2008 | Tkaczyk |
| 2008/0260097 A1 | 10/2008 | Anwar |
| 2008/0304622 A1 | 12/2008 | Morton |
| 2009/0067575 A1 | 3/2009 | Seppi |
| 2009/0086907 A1 | 4/2009 | Smith |
| 2009/0116617 A1 | 5/2009 | Mastronardi |
| 2009/0127459 A1 | 5/2009 | Neustadter |
| 2009/0168964 A1 | 7/2009 | Safai |
| 2009/0238336 A1 | 9/2009 | Akery |
| 2009/0245462 A1 | 10/2009 | Agrawal |
| 2009/0257555 A1 | 10/2009 | Chalmers |
| 2009/0285353 A1 | 11/2009 | Ellenbogen |
| 2009/0316851 A1 | 12/2009 | Oosaka |
| 2010/0020937 A1 | 1/2010 | Hautmann |
| 2010/0161504 A1 | 6/2010 | Casey |
| 2010/0177868 A1 | 7/2010 | Smith |
| 2010/0177873 A1 | 7/2010 | Chen |
| 2010/0295689 A1 | 11/2010 | Armistead |
| 2011/0019797 A1 | 1/2011 | Morton |
| 2011/0019799 A1 | 1/2011 | Shedlock |
| 2011/0038453 A1 | 2/2011 | Morton |
| 2011/0064192 A1 | 3/2011 | Morton |
| 2011/0075808 A1 | 3/2011 | Rothschild |
| 2011/0204243 A1 | 8/2011 | Bendahan |
| 2011/0206179 A1 | 8/2011 | Bendahan .................. 378/19 |
| 2011/0235777 A1 | 9/2011 | Gozani |
| 2011/0266643 A1 | 11/2011 | Engelmann |
| 2012/0076257 A1 | 3/2012 | Star-Lack et al. ............. 378/4 |
| 2012/0099710 A1 | 4/2012 | Kotowski |
| 2012/0104276 A1 | 5/2012 | Miller |
| 2012/0116720 A1 | 5/2012 | Klann |
| 2013/0001048 A1 | 1/2013 | Panesar |
| 2013/0039463 A1 | 2/2013 | Mastronardi et al. ......... 378/57 |
| 2013/0156156 A1 | 6/2013 | Roe et al. .................. 378/57 |
| 2014/0105367 A1 | 4/2014 | Horvarth |
| 2014/0185771 A1 | 7/2014 | Morton |
| 2014/0197321 A1 | 7/2014 | Bendahan |
| 2014/0294147 A1* | 10/2014 | Chen ................... G01V 5/0016 378/57 |
| 2015/0036798 A1 | 2/2015 | Morton |
| 2015/0078519 A1 | 3/2015 | Morton |

(56) References Cited

U.S. PATENT DOCUMENTS

| | | |
|---|---|---|
| 2015/0168589 A1 | 6/2015 | Morton |
| 2015/0301220 A1 | 10/2015 | Morton |
| 2015/0355117 A1 | 12/2015 | Morton |
| 2015/0355369 A1 | 12/2015 | Morton |
| 2016/0025888 A1 | 1/2016 | Peschmann |
| 2016/0025889 A1 | 1/2016 | Morton |
| 2016/0033674 A1 | 2/2016 | Allman |
| 2016/0170077 A1 | 6/2016 | Morton |
| 2016/0223706 A1 | 8/2016 | Franco |
| 2017/0059739 A1* | 3/2017 | Mastronardi ........ G01V 5/0008 |
| 2017/0299526 A1 | 10/2017 | Morton |
| 2017/0299764 A1 | 10/2017 | Morton |
| 2017/0315242 A1 | 11/2017 | Arodzero |
| 2018/0128935 A1 | 5/2018 | Morton |

FOREIGN PATENT DOCUMENTS

| | | |
|---|---|---|
| EP | 1413898 A1 | 4/2004 |
| GB | 2255634 A | 11/1992 |
| GB | 2409268 A | 6/2005 |
| GB | 2424065 A | 9/2006 |
| GB | 2438317 A | 11/2007 |
| WO | 985585 A1 | 12/1998 |
| WO | 2004010127 A1 | 1/2004 |
| WO | 2005098400 A2 | 10/2005 |
| WO | 2006036076 A1 | 4/2006 |
| WO | 2006053279 A2 | 5/2006 |
| WO | 2006078691 A2 | 7/2006 |
| WO | 2007035359 A2 | 3/2007 |
| WO | 2007055720 A2 | 5/2007 |
| WO | 2007068933 A1 | 6/2007 |
| WO | 2007103216 A2 | 9/2007 |
| WO | 2008017983 A2 | 2/2008 |
| WO | 2009106803 A2 | 9/2009 |
| WO | 2009143169 A1 | 11/2009 |
| WO | 2011069024 A1 | 6/2011 |
| WO | 2011091070 A2 | 7/2011 |
| WO | 2013116549 | 8/2013 |
| WO | 2013119423 A1 | 8/2013 |
| WO | 2014107675 | 7/2014 |
| WO | 2014121097 A1 | 8/2014 |
| WO | 2014124152 A2 | 8/2014 |
| WO | 2016011205 | 1/2016 |
| WO | 2018064434 | 4/2018 |

OTHER PUBLICATIONS

International Search Report for PCT/US17/54211, dated Jan. 18, 2018.
CRS Report for Congress, Aviation Security Technologies and Procedures: Screening Passengers and Baggage, Oct. 26, 2001, pp. 1-12.
International Search Report for PCT/US2015/040653, dated Dec. 16, 2015.
International Search Report for PCT/US14/56652, dated Apr. 27, 2015.
International Search Report for PCT/US14/14198, dated May 16, 2014.
International Preliminary Report on Patentability for PCT/US2014/014198, dated Aug. 4, 2015.
International Search Report for PCT/US11/21758; dated Jul. 7, 2011, Rapiscan Systems Inc.
International Preliminary Report on Patentability for PCT/US11/21758, dated Jul. 7, 2011.
Written Opinion on Patentability for PCT/US11/21758; dated Jul. 7, 2011; Rapiscan Systems.
Molchanov P A et al: 'Nanosecond gated optical sensors for ocean optic applications' Sensors Applications Symposium, 2006. Proceedings of the 2006 IEEE Houston, Texas,USA Feb. 7-9, 2006, Piscataway, NJ, USA,IEEE, Feb. 7, 2006 (Feb. 7, 2006) , pp. 147-150, XP010917671 ISBN: 978-0-7803-9580-0.
Mobile X-Ray Inspection Systems, Internet Citation, Feb. 12, 2007, pp. 1-2, URL:http://web.archive.org/web/20070212000928/http://www.bombdetecti- on.com/cat--details.php?catid=20.
International Search Report for PCT/GB09/00575, dated Apr. 7, 2010.
International Search Report for PCT/GB2009/000497, dated Jan. 22, 2010.
Smith C. R. et al: 'Application of 450 kV computed tomography to engine blocks with steel liners' Materials Evaluation vol. 65, No. 5, 2007, pp. 458-461, XP055108238.
International Search Report for PCT/US13/23676, dated Jun. 28, 2013.
International Search Report for PCT/US13/24191, Rapiscan Systems Inc., dated Jun. 25, 2013.
International Search Report for PCT/US2014/010370, dated May 13, 2014.
International Search Report for PCT/US10/58809; Rapiscan Systems Inc.; dated Apr. 19, 2011.
International Search Report for PCT/US2014/015126, dated May 27, 2014.
Written Opinion of the International Searching Authority for PCT/US2014/015126, dated May 27, 2014.

* cited by examiner

RAPIDLY RELOCATABLE MODULAR CARGO CONTAINER SCANNER

The present application claims the priority of U.S. Provisional Patent Application Ser. No. 62/018,787, filed Jun. 30, 2014, which is incorporated herein by reference.

TECHNICAL FIELD

The present invention relates to systems and methods for inspection of cargo using penetrating radiation, and, more particularly to rapidly relocatable systems and methods for scanning cargo containers.

BACKGROUND OF THE INVENTION

Cargo containers are frequently subject to inspection at seaports, and screened for contraband goods or articles of terrorism. One common inspection modality uses X-rays, or other penetrating radiation, to traverse the cargo containers and provide images of the contents of the containers. Prior art systems for inspecting cargo containers using X-rays have employed one of two modalities: In one scenario, the cargo containers are borne on a truck or other engine-propelled conveyance and moved relative to a scanning portal (either free-standing or truck-borne) or gantry in order for X-rays to penetrate the entire height of the containers and be detected in transmission. (Relative motion may be achieved either by moving the cargo relative to a fixed portal, or, equivalently, by moving a gantry relative to a fixed object of inspection.) Alternatively, a truck with a gantry may be moved in an inspection path relative to one or more fixed cargo containers.

An example of a prior art cargo inspection system that is permanently installed is shown in FIG. 1. Cargo containers 10 must be loaded onto a truck 12 and driven through a fixed gantry 14 where X-rays, or other penetrating radiation, derived from a source located in source enclosure 16, is transmitted through the cargo and detected by detectors (not shown) located within the gantry.

A deficiency of the prior art permanent inspection installation depicted in FIG. 1 is that cargo containers 10, to be inspected, must be hauled to a single scanner location. Changes in port layout or flow of commerce may require reinstallation of the entire system which may be very costly and time-consuming.

It would thus be advantageous to inspect cargo containers without the ponderous set-up overhead entailed in erecting and aligning a cargo scanning gantry, and without requiring that containers be trucked through a portal.

SUMMARY OF EMBODIMENTS OF THE INVENTION

In accordance with embodiments of the present invention, a cargo inspection system is provided that has a first lead-in conveyor disposed on a first trailer for receiving a cargo container for inspection and an inspection module disposed on a second trailer for scanning the cargo container with penetrating radiation, detecting penetrating radiation scattered by the cargo container and producing an inspection signal. The cargo inspection system also has an exit conveyor disposed on a third trailer for projecting the cargo container following scanning, and a processor adapted for receiving the x-ray inspection signal over a course of passage of the cargo container through the inspection module and for producing therefrom an image characterizing contents of the cargo container.

In accordance with alternate embodiments of the invention, the inspection module includes an X-ray source, and a transmission detector disposed distal to the cargo container relative to the X-ray source. Alternatively, or additionally, the inspection module includes scatter detector disposed to receive penetrating radiation from the X-ray source that has been scattered by contents of the cargo container.

In another embodiment of the invention, the cargo inspection system may have one or more additional lead-in conveyors, coupled to the first lead-in conveyor, for loading an additional cargo container for subsequent scanning by the inspection module.

In accordance with another aspect of the present invention, a method is provided for inspecting cargo disposed in a cargo container. The method has steps of:
  a. impelling the cargo container on a lead-in conveyor disposed on a first trailer toward an inspection module;
  b. scanning the cargo container with penetrating radiation;
  c. detecting the penetration radiation after interaction with contents of the cargo container to generate an detector signal; and
  d. receiving the x-ray inspection signal over a course of passage of the cargo container through the inspection module and producing therefrom an image characterizing contents of the cargo container.

In further embodiments of the present invention, the step of detecting may include detecting penetration radiation that has traversed the cargo container, or penetrating radiation that has been scattered by contents of the cargo container.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS OF THE INVENTION

Figure 1:
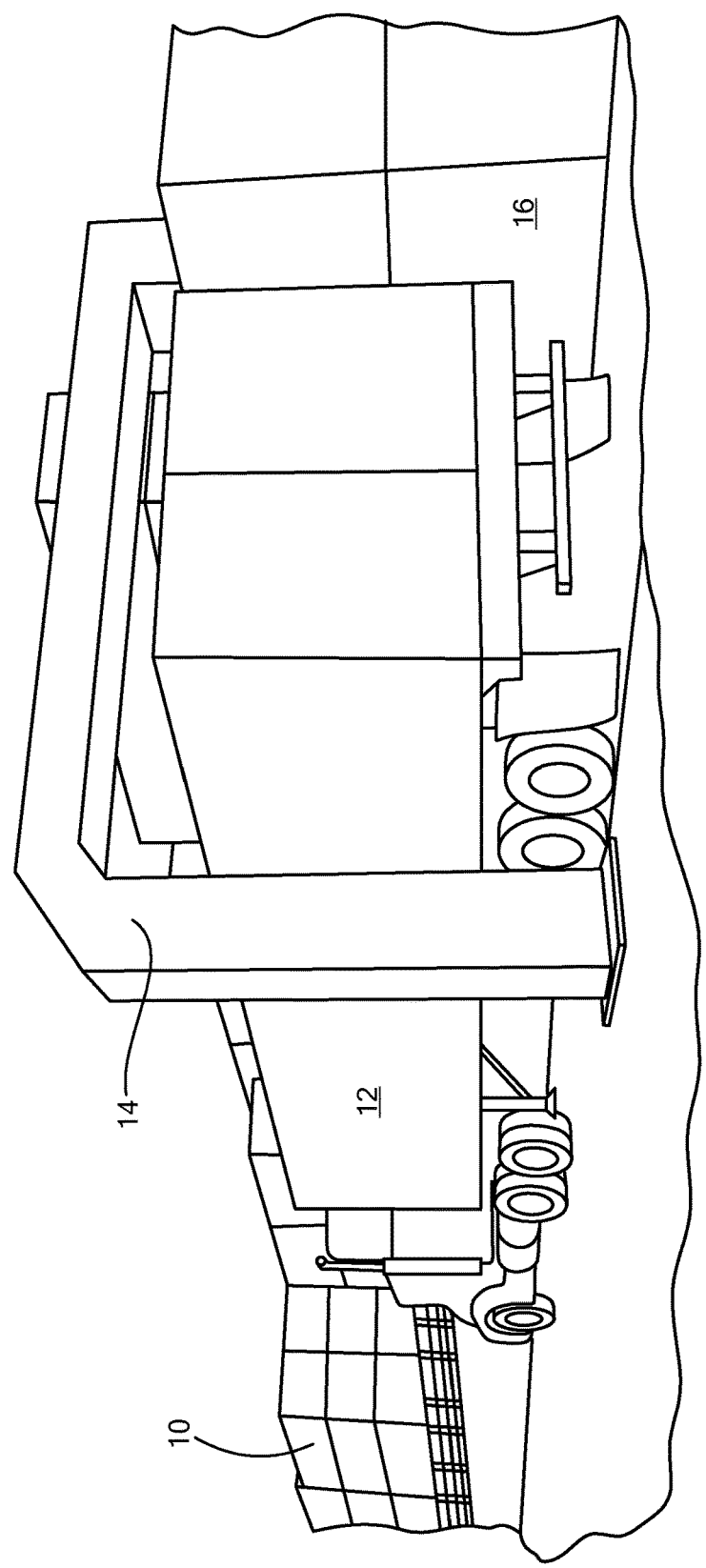
FIG. 1 depicts a typical prior art high-energy transmission X-ray inspection system, in the context of which embodiments of the present invention are advantageously applied.

Definitions: As used herein, and in any appended claims, the term "cargo container" refers to any standardized intermodal freight container meeting any set of international dimensional standards, such as ISO standards, for example. It is to be understood that the use of other modes of cargo packaging, such as pallets or skids, similarly falls within the scope of the present invention, and is encompassed by the use, herein, of the term "cargo container."

A "conveyance" shall be any device characterized by a platform borne on ground-contacting members such as wheels, tracks, treads, skids, etc., used for transporting equipment from one location to another.

The word "conveyor," as used herein and in any appended claims, shall refer to any handling equipment designed and suited for moving a cargo container from one place to another. A conveyor may employ rollers, driven by chains or otherwise, however other conveyor mechanisms are subsumed within the scope of the present invention.

The word "trailer," as used herein and in any appended claims, shall refer to a conveyance adapted to be drawn over an underlying surface by a motorized vehicle that may be referred to herein as a "tractor."

The term "cargo container" shall be used inclusively of its contents.

The term "X-ray source" shall signify a device that produces X-rays, including, without limitation, X-ray tubes, or Bremsstrahlung targets impinged upon by energetic particles, without regard for the mechanism used for acceleration of the particles, including, without limitation, linacs, etc.

The systems and methods described herein may be described in terms of X-rays, however the applicability of the teachings to other spectral ranges is clear, and encompasses, within the scope of the invention, all manner of penetrating radiation.

Methods are well known for inspecting cargo using penetrating radiation (which may be electromagnetic, such as X-rays or gamma rays, or may be comprised of massive particles such as neutrons, etc.). Such radiation emanates from one or more sources and impinges upon an article to be inspected. Similarly well-known methods are used to pass the penetrating radiation through the entire volume of the inspected article (or, else, specified portions thereof). Passing the penetrating radiation through the inspected volume typically entails scanning, which is to say that the entire volume is not irradiated at once. The penetrating radiation is typically formed into a beam, and the beam profile may have various shapes, such as that of a pencil, or a fan, or a cone. In any event, passing the beam through the inspected volume may be referred to as "scanning" Scanning may entail moving the beam, and/or moving the inspected article. A system for moving cargo relative to an inspecting beam of penetrating radiation may be referred to herein as a "scanning system."

Inspection of cargo by means of penetrating radiation transmitted through the cargo, at one range of energies, or at multiple ranges of energies, may be practiced with a single beam or with multiple beams, as described in US Published Patent Application Ser. No. US 2013/0136230 (entitled "System and Methods for Multi-Beam Inspection of Cargo in Relative Motion," and incorporated herein by reference). Additionally, cargo may be inspected using detectors disposed for collecting penetrating radiation that is scattered by the inspect article, or by items disposed therein. Inspection of cargo using one or more scatter detection systems (backscatter, for example) is described in U.S. Pat. No. 7,400,701 (entitled "Backscatter Inspection Portal," and incorporated herein by reference).

Figure 2:
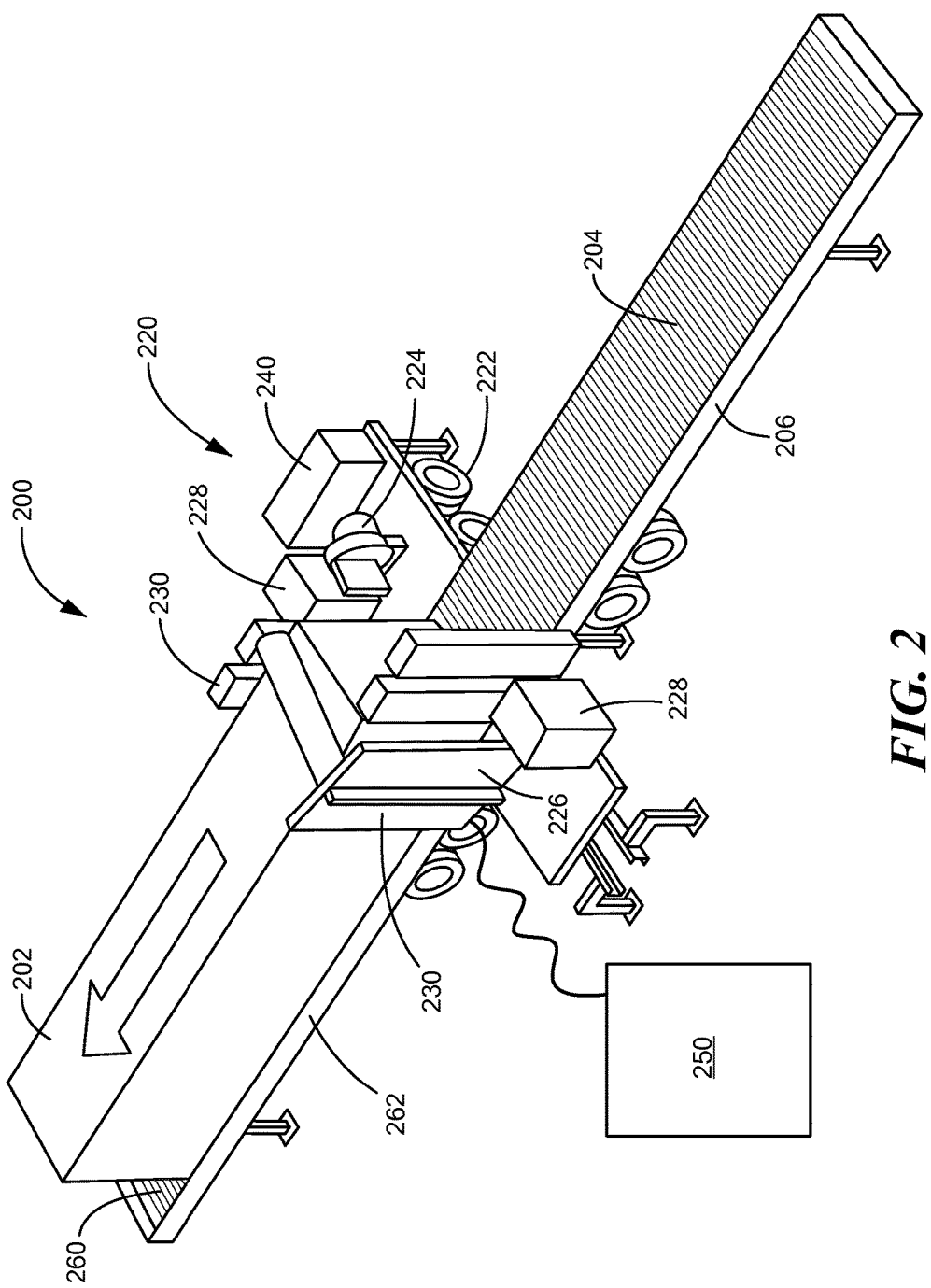
FIG. 2 shows a perspective view of a modular cargo container scanning system, in accordance with an embodiment of the present invention.

Referring to FIG. 2, a scanning system, designated generally by numeral 200, is described in accordance with an embodiment of the present invention. The entirety of the scanning system 200 is assembled for operation from multiple components which are adapted to be coupled to each other using no more than a tractor. A lead-in conveyor 204 serves to impel cargo 202 toward an inspection module 220 and may be any sort of mechanical conveyor suited to convey cargo of the kind being inspected. Lead-in conveyor 204 is disposed on a first trailer 206, allowing it to be drawn by a tractor (not shown) and positioned as part of scanning system 200. In different embodiments of the present invention cargo 202 may be conveyed for inspection either in discrete cargo containers, or stacked in any manner, or loaded onto a conveyance for purposes of transport through scanning system 200.

Inspection module 220 is disposed on a second trailer 222, allowing inspection module 220 to be drawn by a tractor (not shown) and positioned as part of scanning system 200. Inspection module 220 contains either a transmission inspection unit or a backscatter inspection unit, or both. The transmission inspection unit has a source 224 and a transmission detection module 226, which may include one or more transmission detectors. Source 224 may be referred to herein, for convenience and without loss of generality, as an "X-ray source."

Each backscatter inspection unit has a source 228 and one or more scatter detectors 230 for detecting penetrating radiation that has been scattered by contents of the cargo container 10. A beam stop 232 may be provided to reduce or eliminate ambient exposure to penetrating radiation. Electrical power is provided by a generator 240, allowing for the scanning system 200 to be self-contained and readily moved. While any source 224 of penetrating radiation may be used within the scope of the present invention, a low-output linac or betatron is preferred, in certain embodiments, for their small footprint. Detectors 226 and 230 produce inspection signals which are received by processor 250 over the course of passage of the cargo container 10 through the inspection module 226. Processor 250 generates images or other diagnostics of the contents of cargo container 10. Data from scanning system 200 may be conveyed, by cable or wirelessly, to a nearby van, for example, where processor 250 may be housed, as may be an operator or image analyst.

Cargo container 10, after scanning at inspection module 226, is impelled away from the inspection module 220 by an exit conveyor 260 disposed on a third trailer 262. The three trailers 206, 222, and 262 may be readily and quickly repositioned by a tractor truck, and the lead-in conveyor 204 and exit conveyor 260 may be readily coupled to inspection module 220 using standard coupling mechanisms.

Figure 3:
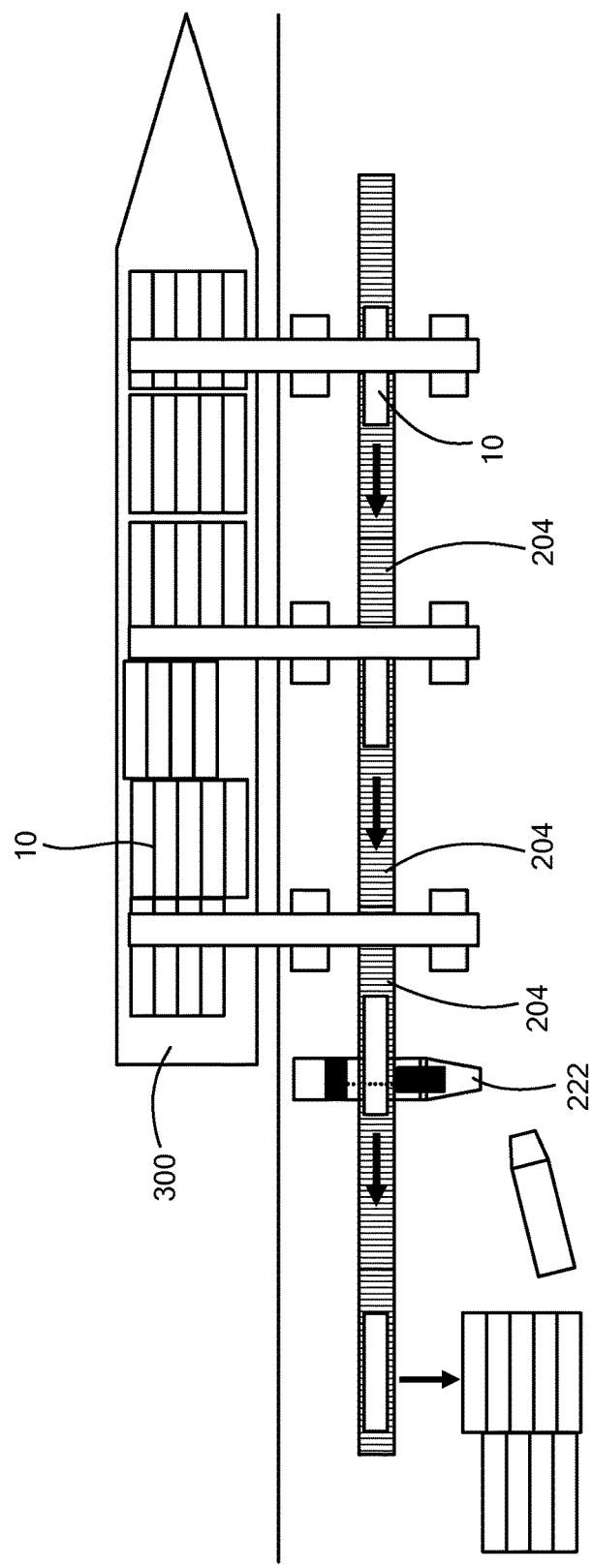
FIG. 3 depicts a schematic top view of a multiple modular cargo container scanning systems with multiple conveyor units, employed in tandem in the offloading of a shipping vessel, in accordance with another embodiment of the present invention.

In accordance with another embodiment of the present invention, described with reference to FIG. 3, elements of scanning system 200 (shown in FIG. 2) may be multiplexed to increase throughput. Thus, for example, multiple lead-in conveyors 204 may receive cargo containers 10 off-loaded from shipping vessel 300, and feed them past scanning module 222 for inspection using penetrating radiation.

A scanning system in accordance with any of the embodiments of the present invention described herein, may advantageously be moved from one location to another in a matter of minutes or hours. Additional advantages accrue from the fact that the containers need not be loaded onto trucks, nor do drivers need to move in and out of their vehicles, or otherwise add time to the scanning operation. Moreover, scanning is more efficient with the present invention, since only the container is scanned, rather than a larger truck.

Where examples presented herein involve specific combinations of method acts or system elements, it should be understood that those acts and those elements may be combined in other ways to accomplish the same objectives of modular inspection with penetrating radiation. Additionally, single device features may fulfill the requirements of separately recited elements of a claim. The embodiments of the invention described herein are intended to be merely exemplary; variations and modifications will be apparent to those skilled in the art. All such variations and modifications are intended to be within the scope of the present invention as defined in any appended claims.

What is claimed is:

1. A cargo inspection system, the system comprising:
a first lead-in conveyor disposed on a first trailer for receiving a cargo container for inspection;
an inspection module disposed on a second trailer distinct from the first trailer for scanning the cargo container with penetrating radiation, detecting penetrating radiation that has interacted with the cargo container, and producing an inspection signal;
an exit conveyor disposed on a third trailer distinct from the second trailer and the first trailer for impelling the cargo container following scanning; and
a processor adapted for receiving the inspection signal over a course of passage of the cargo container through the inspection module and for producing therefrom an image characterizing contents of the cargo container.

2. A cargo inspection system in accordance with claim 1, wherein the inspection module includes an X-ray source.

3. A cargo inspection system in accordance with claim 2, wherein the inspection module includes a transmission detector disposed distal to the cargo container relative to the X-ray source.

4. A cargo inspection system in accordance with claim 2, wherein the inspection module includes a scatter detector disposed to receive penetrating radiation from the X-ray source that has been scattered by contents of the cargo container.

5. A cargo inspection system in accordance with claim 1, further comprising a second lead-in conveyor, coupled to the first lead-in conveyor, for loading an additional cargo container for subsequent scanning by the inspection module.

6. A method for inspecting cargo disposed in a cargo container, the method comprising:
impelling the cargo container on a lead-in conveyor disposed on a first trailer toward an inspection module disposed on a second trailer distinct from the first trailer;
scanning the cargo container with penetrating radiation;
detecting the penetration radiation after interaction with contents of the cargo container to generate a detector signal;
impelling the cargo container on an exit conveyor disposed on a third trailer distinct from the second trailer and the first trailer following scanning; and
receiving the detector signal over a course of passage of the cargo container through the inspection module and producing therefrom an image characterizing contents of the cargo container.

7. A method for inspecting cargo in accordance with claim 6, wherein detecting includes detecting penetration radiation that has traversed the cargo container.

8. A method for inspecting cargo in accordance with claim 7, wherein detecting includes detecting penetration radiation scattered by contents of the cargo container.

9. A cargo inspection system, the system comprising:
a first lead-in conveyor disposed on a first conveyance for receiving a cargo container for inspection;
an inspection module disposed on a second conveyance distinct from the first conveyance for scanning the cargo container with penetrating radiation, detecting penetrating radiation that has interacted with the cargo container, and producing an inspection signal;
an exit conveyor, distinct from the first lead-in conveyor, disposed on a third conveyance distinct from the second conveyance and the first conveyance for impelling the cargo container following scanning; and
a processor adapted for receiving the inspection signal over a course of passage of the cargo container through the inspection module and for producing therefrom an image characterizing contents of the cargo container.

10. The cargo inspection system of claim 9, wherein the inspection module includes an X-ray source.

11. The cargo inspection system of claim 10, wherein the inspection module includes a transmission detector disposed distal to the cargo container relative to the X-ray source.

12. The cargo inspection system of claim 10, wherein the inspection module includes a scatter detector disposed to receive penetrating radiation from the X-ray source that has been scattered by contents of the cargo container.

13. The cargo inspection system of claim 9, further comprising a second lead-in conveyor, coupled to the first lead-in conveyor, for loading an additional cargo container for subsequent scanning by the inspection module.

14. A method for inspecting cargo disposed in a cargo container, the method comprising:
impelling the cargo container on a lead-in conveyor disposed on a first conveyance toward an inspection module disposed on a second conveyance distinct from the first conveyance;
scanning the cargo container with penetrating radiation;
detecting the penetration radiation after interaction with contents of the cargo container to generate a detector signal;
receiving the detector signal over a course of passage of the cargo container through the inspection module;
impelling the cargo container on an exit conveyor, distinct from the lead-in conveyor, disposed on a third conveyance distinct from the second conveyance and the first conveyance following scanning; and
producing an image from the detector signal, wherein the image characterizes contents of the cargo container.

15. The method of claim 14, wherein the inspection module includes an X-ray source.

16. The method of claim 15, wherein the inspection module includes a transmission detector disposed distal to the cargo container relative to the X-ray source.

17. The method of claim 15, wherein the inspection module includes a scatter detector disposed to receive penetrating radiation from the X-ray source that has been scattered by contents of the cargo container.

18. The method of claim 14, further comprising coupling a second lead-in conveyor to the first lead-in conveyor, wherein the second lead-in conveyor is configured to load an additional cargo container for subsequent scanning by the inspection module.

19. The method of claim 14, further comprising separately positioning the first conveyance, second conveyance, and the third conveyance such that the second conveyance may be coupled to each of the first conveyance and the third conveyance.

* * * * *